US00PP32069P2

(12) United States Plant Patent
Gass

(10) Patent No.: US PP32,069 P2
(45) Date of Patent: Aug. 11, 2020

(54) ***HESPERALOE* PLANT NAMED 'MSWNNUEVO LEON'**

(50) Latin Name: *Hesperaloe campanulata*
Varietal Denomination: MSWNNuevo Leon

(71) Applicant: Ronald E. Gass, Glendale, AZ (US)

(72) Inventor: Ronald E. Gass, Glendale, AZ (US)

(73) Assignee: Camelot Nurseries Inc., Glendale, AZ (US)

( * ) Notice: Subject to any disclaimer, the term of this patent is extended or adjusted under 35 U.S.C. 154(b) by 0 days.

(21) Appl. No.: 16/602,182

(22) Filed: Aug. 23, 2019

(51) Int. Cl.
*A01H 5/02* (2018.01)
*A01H 6/12* (2018.01)

(52) U.S. Cl.
USPC ..... Plt./373

(58) Field of Classification Search
USPC ..... Plt./373
CPC ..... A01H 5/02; A01H 6/12
See application file for complete search history.

*Primary Examiner* — Annette H Para
(74) *Attorney, Agent, or Firm* — C. A. Whealy

(57) ABSTRACT

A new and distinct cultivar of *Hesperaloe* plant named 'MSWNNuevo Leon', characterized by its upright and tall plant habit; vigorous growth habit; strong and upright green-colored peduncles that are uniformly branched; relatively large campanulate red purple and light red purple bi-colored flowers; relatively long flowering period; and good garden and landscape performance.

2 Drawing Sheets

Botanical designation: *Hesperaloe campanulata.*
Cultivar denomination: 'MSWNNuevo Leon'.

BACKGROUND OF THE INVENTION

The present invention relates to a new and distinct cultivar of *Hesperaloe* plant, botanically known as *Hesperaloe campanulata* and hereinafter referred to by the name 'MSWNNuevo Leon'.

The new *Hesperaloe* plant is a product of a planned breeding program conducted by the Inventor in Glendale, Ariz. The objective of the breeding program is to develop new freely flowering *Hesperaloe* plants with unique flower form and color, good landscape and garden performance, drought tolerance and high temperature tolerance.

The new *Hesperaloe* plant originated from a self-pollination during the spring of 1991 of an unnamed selection of *Hesperaloe campanulata*, not patented. The new *Hesperaloe* plant was discovered and selected by the Inventor as a single flowering plant within the progeny of the stated self-pollination in a controlled environment in Glendale, Ariz. in May, 2008.

Asexual reproduction of the new *Hesperaloe* plant by in vitro meristem culture since the spring of 2016 in a controlled greenhouse environment in Grand Haven, Mich., has shown that the unique features of this new *Hesperaloe* plant are stable and reproduced true to type in successive generations of asexual reproduction.

SUMMARY OF THE INVENTION

Plants of the new *Hesperaloe* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'MSWNNuevo Leon'. These characteristics in combination distinguish 'MSWNNuevo Leon' as a new and distinct *Hesperaloe* plant:

1. Upright and tall plant habit.
2. Vigorous growth habit.
3. Strong and upright green-colored peduncles that are uniformly branched.
4. Relatively large campanulate red purple and light red purple bi-colored flowers.
5. Relatively long flowering period.
6. Good garden and landscape performance.

Plants of the new *Hesperaloe* can be compared to plants of the parent selection. Plants of the new *Hesperaloe* differ from plants of the parent selection in the following characteristics:

1. Plants of the new *Hesperaloe* are uniform in height whereas plants of the parent selection are not uniform in height.
2. Plants of the new *Hesperaloe* have uniformly branched peduncles whereas plants of the parent selection have inconsistently branched peduncles.
3. Plants of the new *Hesperaloe* have larger flowers than plants of the parent selection.
4. Plants of the new *Hesperaloe* flower more uniformly and more freely than plants of the parent selection.
5. Flowers of plants of the new *Hesperaloe* are red purple and light red purple bi-colored whereas flowers of plants of the parent selection are soft pink in color.

Plants of the new *Hesperaloe* can also be compared to plants of *Hesperaloe funifera* x *Hesperaloe parviflora* 'Perfu', disclosed in U.S. Plant Pat. No. 21,728. Plants of the new *Hesperaloe* differ primarily from plants of 'Perfu' in the following characteristics:

1. Plants of the new *Hesperaloe* have uniformly branched peduncles whereas plants of 'Perfu' have inconsistently branched or non-branched peduncles.

2. Plants of the new *Hesperaloe* have larger flowers than plants of 'Perfu'.
3. Plants of the new *Hesperaloe* flower more uniformly and more freely than plants of 'Perfu'.
4. Flowers of plants of the new *Hesperaloe* are red purple and light red purple in color whereas flowers of plants of 'Perfu' are pink in color.

BRIEF DESCRIPTION OF THE PHOTOGRAPHS

The accompanying colored photographs illustrate the overall appearance of the new *Hesperaloe* plant, showing the colors as true as it is reasonably possible to obtain in colored reproductions of this type. Colors in the photographs may differ slightly from the color values cited in the detailed botanical description which accurately describe the colors of the new *Hesperaloe* plant.

The photograph on the first sheet is a side perspective view of typical plants of 'MSWNNuevo Leon' grown in containers.

The photograph on the second sheet is a close-up view of a typical inflorescence of 'MSWNNuevo Leon'.

DETAILED BOTANICAL DESCRIPTION

The aforementioned photographs and following observations, measurements and values describe plants of the new *Hesperaloe* grown during the spring and early summer in five-gallon containers in an outdoor nursery in Glendale, Ariz. and under cultural practices and conditions which closely approximate commercial production. During the production of the plants, day temperatures ranged from 7.2° C. to 53.8° C. and night temperatures ranged from 3.8° C. to 33.3° C. Plants were three years old when the photographs and the description were taken. In the description, color references are made to The Royal Horticultural Society Colour Chart, 2015 Edition, except where general terms of ordinary dictionary significance are used.

Botanical classification: *Hesperaloe campanulata* 'MSWNNuevo Leon'.

Parentage:

*Female, or seed, parent*.—Unnamed selection of *Hesperaloe campanulata*, not patented.

*Male, or pollen, parent*.—Unnamed selection of *Hesperaloe campanulata*, not patented.

Propagation:

*Type*.—By in vitro meristem culture.

*Time to initiate roots, summer*.—About two weeks with ambient temperatures about 38° C. to 48° C.

*Time to initiate roots, winter*.—About three weeks with ambient temperatures about 10° C. to 24° C.

*Time to produce a rooted young plant, summer*.—About two months with ambient temperatures about 38° C. to 48° C.

*Time to produce a rooted young plant, winter*.—About four months with ambient temperatures about 10° C. to 24° C.

*Root description*.—Medium in thickness, fleshy; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant form and growth habit*.—Perennial subshrub; upright and tall plant habit; vigorous growth habit; leaves arranged in a basal rosette with a strong, upright and uniformly branched central flower stalk.

*Plant height, from soil level to top of inflorescence*.—About 212 cm.

*Plant height, from soil level to top of foliar plane*.—About 107 cm.

*Plant diameter* (*area of spread*).—About 51 cm.

Stem description:

*Internode length*.—About 1.5 cm.

*Aspect*.—Upright.

*Texture*.—Smooth, glabrous.

*Color*.—Close to 153A; leaves cover the stem.

Leaf description:

*Arrangement*.—In a basal rosette, whorled; simple; sessile.

*Length*.—About 110 cm.

*Width*.—At the apex, about 1 mm; mid-section, about 1.2 cm; at the base, about 3 cm.

*Shape*.—Acicular; concave.

*Apex*.—Acuminate; apices are sharply pointed.

*Base*.—Clasping the stem.

*Margin*.—Entire; filiferous with tough curly fibers, close to NN155D in color.

*Texture and luster, upper and lower surfaces*.—Smooth, glabrous; tough, rigid and fibrous; longitudinally and minutely ridged; somewhat succulent; slightly glossy.

*Venation pattern*.—Parallel.

*Color*.—Developing and fully developed leaves, upper surface: Close to 146A; venation, close to 146A. Developing and fully developed leaves, lower surface: Close to 146A to 146B; venation, close to 146A to 146B.

Flower description:

*Flower type, arrangement and flowering habit*.—Single campanulate flowers; flowers arranged in terminal, upright and uniformly branched racemes; freely flowering habit with about 360 flowers per inflorescence at one time; flowers initially face upright to outwardly.

*Natural flowering season*.—Continuous flowering during the spring and summer in Arizona.

*Flower longevity*.—Individual flowers last about five days on the plant; flowers not persistent.

*Fragrance*.—None detected.

*Inflorescence length, including peduncle*.—About 207 cm.

*Inflorescence length, central branched section with flowers*.—About 63 cm.

*Inflorescence length, lateral branched sections with flowers*.—About 42 cm.

*Inflorescence diameter*.—About 7 cm.

*Flower length*.—About 3 cm.

*Flower diameter*.—About 8 mm.

*Flower buds*.—Length: About 9 mm. Diameter: About 5 mm. Shape: Ovoid. Color: Close to 62A.

*Flower segments*.—Quantity and arrangement: Six segments per flower arranged in two whorls. Length: About 3 cm. Width: About 7 mm. Shape: Elliptical, narrow. Apex: Acute; outwardly flared. Base: Truncate, fused. Margin: Entire. Texture and luster, upper surface: Smooth, glabrous; slightly succulent;

slightly glossy. Texture and luster, lower surface: Smooth, glabrous; slightly succulent; matte. Color: When opening and fully opened, upper or inner surface: Close to 62A to 62B; towards the margins and apex, close to 65D; color does not change with development. When opening and fully opened, lower or outer surface: Close to 62A; towards the margins and apex, close to 65D; color does not change with development.

*Peduncles*.—Length, to base of branching: About 140 cm. Length, central branches: About 63 cm. Length, lateral branches: About 42 cm. Diameter: About 1.2 cm. Strength: Strong, sturdy. Aspect: Upright. Texture and luster: Smooth, glabrous; slightly glossy. Color: Close to 146B.

*Pedicels*.—Length: About 1 cm. Diameter: About 1 mm. Strength: Strong, flexible. Aspect: About 45° from peduncle axis. Texture and luster: Smooth, glabrous; matte. Color: Close to N144A.

*Reproductive organs*.—Androecium: Quantity per flower: About six. Filament length: About 1 cm. Filament color: Close to NN155D. Anther shape: Oblong. Anther length: About 5 mm. Anther color: Close to N144A. Amount of pollen: Scarce. Pollen color: Close to N144B. Gynoecium: Quantity per flower: One. Pistil length: About 2.4 cm. Style length: About 1.6 cm. Style color: Close to NN155D. Stigma appearance: Rounded. Stigma color: Close to NN155D. Ovary color: Close to 154D.

*Fruits*.—Type: Shape: Three-segmented, roughly spherical. Length: About 3 cm. Diameter: About 2.8 cm. Texture and luster: Smooth, glabrous; slightly glossy. Color: Close to between 144A and 146A.

*Seeds*.—Quantity per fruit: Numerous, about 126 per fruit. Shape: Semi-circular, flat. Length: About 1 cm. Diameter: About 4.5 mm. Texture and luster: Smooth, glabrous; slightly glossy. Color: Close to 202A.

Garden performance: Plants of the new *Hesperaloe* have been observed to have good garden performance and to be suitable for USDA Hardiness Zones 7 to 11.

Pathogen & pest tolerance: To date, plants of the new *Hesperaloe* have not been observed to be tolerant to pathogens and pests common to *Hesperaloe* plants.

It is claimed:

1. A new and distinct *Hesperaloe* plant named 'MSWN-Nuevo Leon' as illustrated and described.

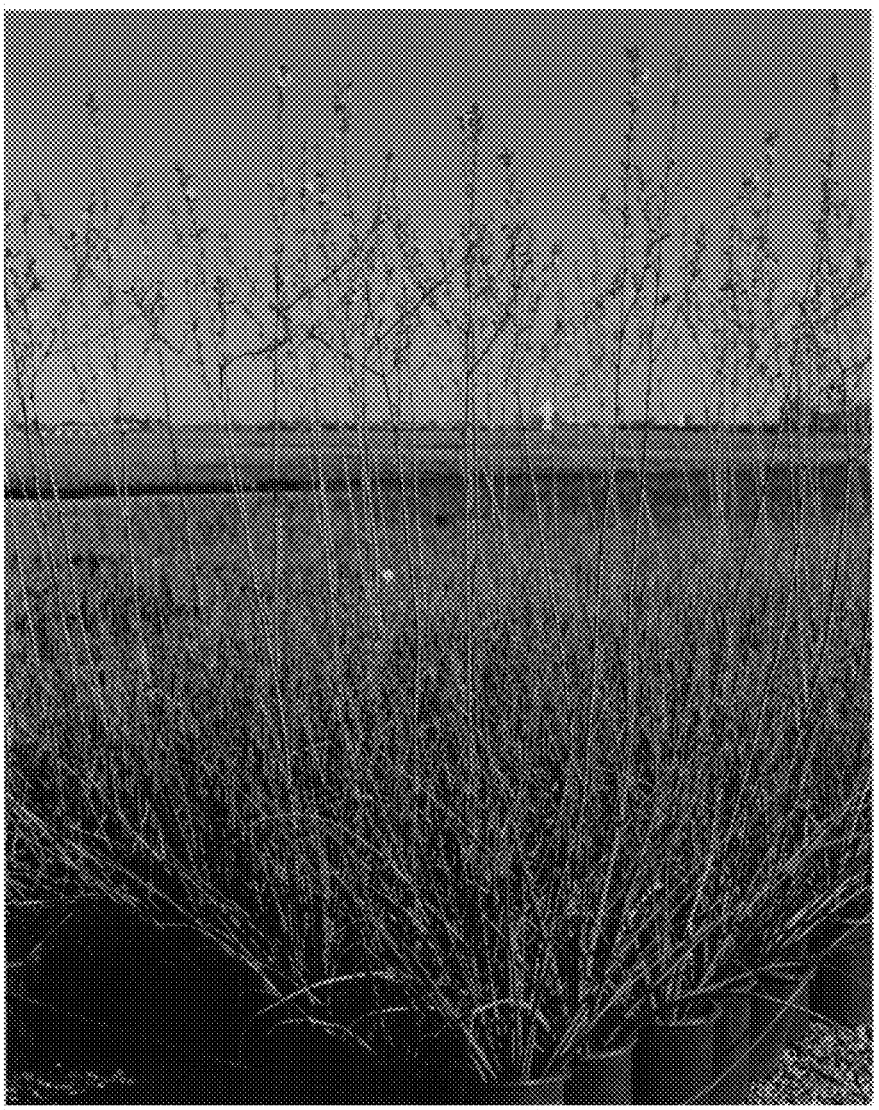

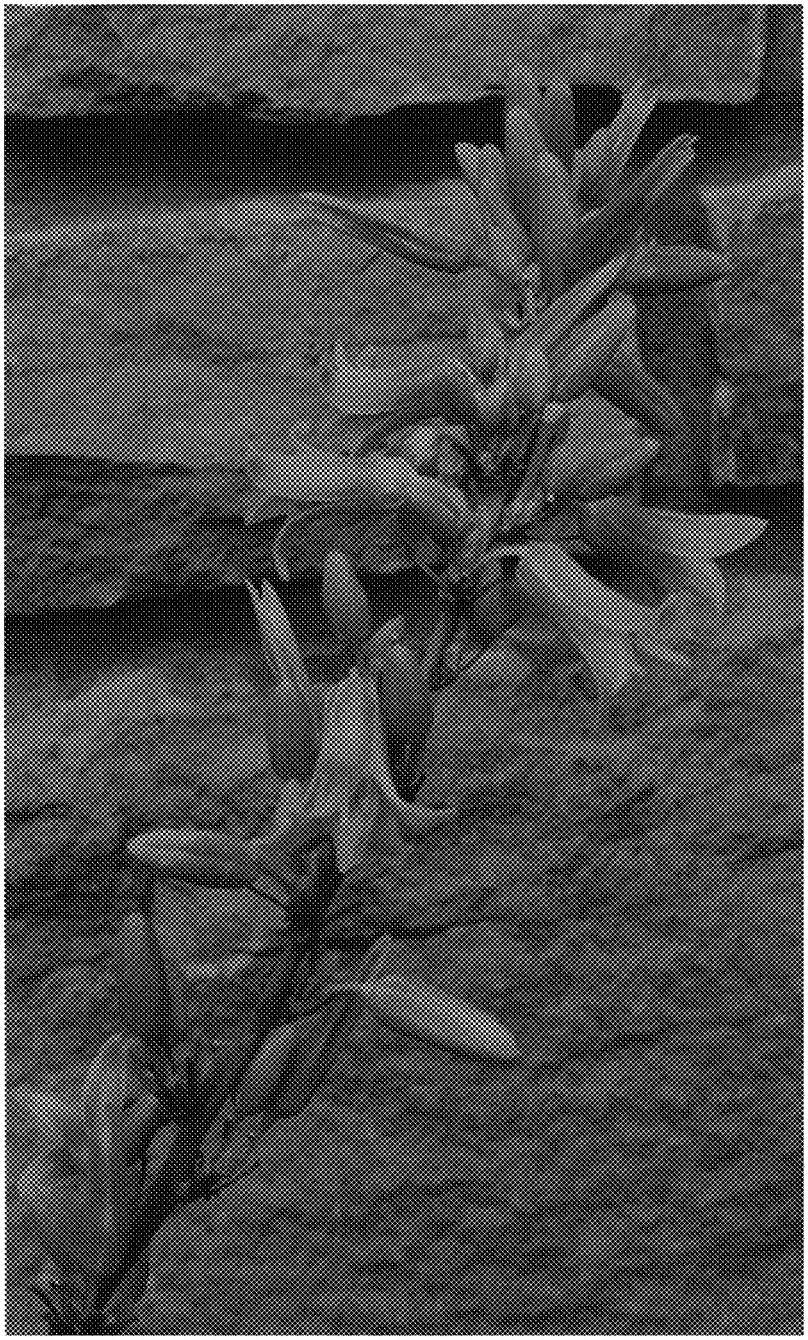

* * * * *